United States Patent

Tienboon

Patent Number: 5,861,041
Date of Patent: Jan. 19, 1999

[54] INTERVERTEBRAL DISK PROSTHESIS AND METHOD OF MAKING THE SAME

[75] Inventor: Prakit Tienboon, 872 Polthep, Phatthanakarn Road, Suan Loang Pravait, Bangkok, Thailand

[73] Assignees: Arthit Sitiso, Lakeview Terrace; Frank Bailly, San Pedro; John Wagner, Calabasas, all of Calif.; Pibul Itiravivong, Bangkok, Thailand; Somsak Kuptniratsaikul, Talingcharn, Thailand; Tawechai Tejapongvorachai; Prakit Tienboon, both of Bangkok, Thailand

[21] Appl. No.: 835,342

[22] Filed: Apr. 7, 1997

[51] Int. Cl.$^6$ .................................................. A61F 2/44
[52] U.S. Cl. ............................................ 623/17; 606/61
[58] Field of Search ........................ 623/16, 17; 606/61, 606/69, 71, 72, 73

[56] References Cited

U.S. PATENT DOCUMENTS

| | | | |
|---|---|---|---|
| 4,904,261 | 2/1990 | Dove et al. | 623/17 |
| 5,062,850 | 11/1991 | MacMillan et al. | 623/17 |
| 5,192,327 | 3/1993 | Brantigan | 623/17 |
| 5,397,364 | 3/1995 | Kozak et al. | 606/61 |
| 5,522,899 | 6/1996 | Michelson | 623/17 |
| 5,571,192 | 11/1996 | Schonhoffer | 623/17 |
| 5,607,424 | 3/1997 | Tropiano | 606/61 |
| 5,609,637 | 3/1997 | Biedermann et al. | 623/17 |
| 5,658,336 | 8/1997 | Pisharodi | 623/17 |

*Primary Examiner*—Paul B. Prebilic
*Assistant Examiner*—Bruce E. Snow
*Attorney, Agent, or Firm*—John J. Posta, Jr.

[57] ABSTRACT

An intervertebral disk prosthesis for implantation between two adjacent vertebrae is disclosed which is more easily implantable intermediate the adjacent vertebrae, particularly from a posterior surgical approach, due to the two-piece construction of the intervertebral disk prosthesis. The intervertebral disk prosthesis of the present invention consists of first and second intervertebral disk segments which, when connected together by a bolt, together form a substantially elliptical configuration of a size fitting between the endplates of two adjacent vertebrae to maintain them in a properly spaced-apart and stable configuration which will be resistive to normal compressive forces exerted on the spine. Large apertures extending through the first and second intervertebral segments may be packed with bone chips or marrow prior to being implanted to facilitate bone ingrowth therethrough to fuse the aforesaid vertebrae together.

21 Claims, 2 Drawing Sheets

INTERVERTEBRAL DISK PROSTHESIS AND METHOD OF MAKING THE SAME

BACKGROUND OF THE INVENTION

Field of the Invention

The present invention relates generally to prosthetic devices for implantation between adjacent vertebrae to treat patients with ruptured or severely degenerated intervertebral disks, and more particularly to a more easily implantable two-piece intervertebral disk prosthesis for insertion intermediate two adjacent vertebrae to maintain the aforesaid vertebrae in a properly spaced-apart and stable configuration which will be resistive to normal compressive forces exerted on the spine while bony integration is occurring to fuse the aforesaid vertebrae together.

The main structural support of the human skeleton is the spinal column, a bony column that consists of a plurality of vertebrae which are interlinked by flexible joints, spaced apart by gelatinous intervertebral disks of fibrocartilage, and held together by ligaments. Each vertebra has a roughly cylindrical body, with wing-like projections, and a bony arch. The arches, which are positioned next to one another, create a tunnel-like space which houses the spinal cord. The cylindrical bodies of the vertebrae are spaced apart by intervertebral disks, and bear most of the compressive load of the spinal column (approximately 80 percent of the total load).

One of the primary causes of back of neck and back pain in patients is when one of these intervertebral disks becomes degenerated or ruptured, no longer spacing the adjacent vertebrae on opposite sides of the intervertebral disk properly apart. When an intervertebral disk becomes degenerated or ruptured to the point where it no longer functions properly, a diskectomy, i.e. removal of the degenerated or ruptured disk from its location between adjacent vertebrae, is indicated, and this treatment has become the classic treatment for the dysfunctional disk.

Following the diskectomy, the two adjacent vertebrae on opposite sides of the removed disk are typically fused together in a process which has as its objective surgically reconstructing the space intermediate the two vertebrae. Two different techniques may be utilized to perform this surgical reconstruction of the intervertebral space. These first of these two techniques is the placement of an autograft, i.e. a bone graft, intermediate the two vertebrae, and the second technique is the installation of an intervertebral prosthesis intermediate the two vertebrae.

The use of autografts has been well established, and the procedure places the autograft between the superior endplate of one vertebra and the inferior endplate of the second vertebra. The autograft bears weight between the two vertebrae, and ultimately fusion occurs between the two vertebrae and the autograft. The material for the autograft may be either material excised from the patient's own fibula or pelvis, and shaped by the surgeon to fit in the intervertebral space. Alternately, an allograft, which is bone which typically has been harvested from a deceased donor, may be specially prepared and sterilized, and then shaped by the surgeon to fit properly.

The alternative to the use of autografts is the use of prosthetic intervertebral implants, which are typically made of titanium and, in some cases, graphite. A wide variety of intervertebral implants have been proposed, most of which require complex installation procedures. These prosthetic devices include wedges, solid cylinders, hollow cylinders, and complex multi-component devices having a number of specially machined parts. Many of these prosthetic devices require special preparation of the two vertebrae between which the intervertebral disk was removed, with such preparation including precision drilling or shaving of the vertebrae to create various apertures, grooves, sockets, etc.

Placement of the prosthetic devices into the intervertebral area may also be a difficult and time consuming process, particularly if the surgery is performed from the posterior side of the spine. This is due to the simple fact that the endplates of the vertebrae are located on the anterior-facing side of the spine, with the spinal cord located between the back (from which the surgical approach is typically made) and the endplates of the vertebrae.

Thus, it will be appreciated by those skilled in the art that if the intervertebral prosthesis is to be inserted from the posterior, it may be difficult to maneuver the prosthesis into place. While the cervical and lumbar regions of the spine may be reached from an anterior position, the thoracic region of the spine is almost always accessed from the posterior position. Thus, many of the intervertebral prostheses previously known are simply less than ideal since they are quite difficult to properly place.

In addition, many of the intervertebral prostheses known in the art also require a great deal of vertebrae preparation. Some of these prostheses require that the facing endplates of the vertebrae be drilled and/or milled to precise shapes, while others require angles of approach which are quite difficult to attain, even when the surgeon is highly skilled in the procedure. Many of these intervertebral prostheses are far from ideal in construction and reliability, and a number of them simply fail over time since they do not adequately facilitate bone ingrowth.

It is accordingly the primary objective of the present invention that it provide an improved intervertebral disk prosthesis which may be used to replace an excised intervertebral disk and restore proper spacing between adjacent vertebrae which have had the intervertebral disk removed. It is an objective of the intervertebral disk prosthesis of the present invention that be of a design and physical configuration which may be easily installed in place intermediate the endplates of two adjacent vertebrae via a posterior surgical approach. It is a related objective of the intervertebral disk prosthesis of the present invention that it not require extensive drilling or other precision shaping of the endplates of the adjacent vertebrae prior to installation. It is also an objective of the intervertebral disk of the present invention that the implant procedure not require the use of complex tools to install and position the intervertebral disk prosthesis intermediate the two vertebrae.

It is an further objective of the intervertebral disk prosthesis of the present invention that it be implantable in a surgical procedure reducing both the trauma to the patient and the time for the surgeon to implant the device. It is also an objective of the intervertebral disk prosthesis of the present invention that it be highly resistive to dislodgement once it is initially installed intermediate two vertebrae. It is yet another objective of the intervertebral disk prosthesis of the present invention that it promote prompt and permanent ingrowth of bone material intermediate the two adjacent vertebrae to facilitate permanent fusion of the aforesaid vertebrae. Still further objectives of the intervertebral disk prosthesis of the present invention are that it be made of biocompatible material compatible with long term implant in the human body, and that it be available in different sizes and configurations to fit a wide variety of patients and different disk locations in the spine.

The intervertebral disk of the present invention must be of a construction which is both durable and long lasting, and it must require no maintenance once it is implanted. In order to enhance the market appeal of the intervertebral disk prosthesis of the present invention, it should also be of a simple mechanical design and relatively inexpensive construction to thereby afford it the broadest possible market. Finally, it is also an objective that all of the aforesaid advantages and objectives of the intervertebral disk prosthesis of the present invention be achieved without incurring any substantial relative disadvantage.

SUMMARY OF THE INVENTION

The disadvantages and limitations of the background art discussed above are overcome by the present invention. With this invention, a two-piece intervertebral disk prosthesis is used to make the prosthesis easier to implant, particularly from a posterior surgical approach. The intervertebral disk prosthesis of the present invention does not require that the endplates of the adjacent vertebrae be prepared prior to installation. Rather, once the ruptured or degenerated intervertebral disk is removed from between the two vertebrae, the intervertebral disk prosthesis of the present invention may be installed.

The intervertebral disk prosthesis of the present invention consists of first and second intervertebral disk segments which, when connected together, define in plan view (from the superior or inferior sides of the prostheses, as installed) a substantially elliptical configuration of a size to fit between the endplates of two adjacent vertebrae. When assembled, the intervertebral disk prosthesis of the present invention is somewhat smaller in size than the endplates of the vertebrae.

The first intervertebral disk segment extends laterally for the entire lateral width of the intervertebral disk prostheses (as installed), and is over half of the height (anterior to posterior, as installed) of the intervertebral disk prostheses. The side of the first intervertebral disk segment which will face the second intervertebral disk segment when the intervertebral disk prostheses is assembled together may be thought of as essentially flat, with a rounded bump protruding outwardly from the flat side at the center thereof. The first intervertebral disk segment has a large aperture extending therethrough from the superior to inferior sides thereof, with the aperture having an essentially semi-elliptical configuration.

The large aperture extending through the first intervertebral disk segment may be packed with bone chips or marrow prior to being implanted to facilitate bone ingrowth. The first intervertebral disk segment has a plurality of blood holes extending through the lateral and anterior sides thereof, which blood holes are thereby in fluid communication with the large aperture extending through the first intervertebral disk segment.

The side of the second intervertebral disk segment which will face the first intervertebral disk segment when the intervertebral disk prostheses is assembled together is contoured to closely fit the contour of the first intervertebral disk segment when the second intervertebral disk segments is assembled thereto. The second intervertebral disk segment has two large apertures extending therethrough from the superior to inferior sides thereof, with the large apertures being respectively located on the left and right sides of the second intervertebral disk segment (as it is installed).

The two large apertures extending through the second intervertebral disk segment may also be packed with bone chips or marrow prior to being implanted to facilitate bone ingrowth. The second intervertebral disk segment also has a plurality of blood holes extending through the lateral and anterior sides thereof, which blood holes are thereby in fluid communication with the two large apertures extending through the second intervertebral disk segment.

The second intervertebral disk segment has axially aligned aperture segments extending therethrough from a location intermediate either the left or right side and the posterior side thereof toward the center of the ellipse defined by the first and second intervertebral disk segments when they are assembled together. The first intervertebral disk segment has a threaded aperture extending through the portion thereof from which the rounded bump protrudes. When the first and second intervertebral disk segments are assembled together, a bolt extends through the aperture segments in the second intervertebral disk segment and is screwed into the threaded aperture in the first intervertebral disk segment. The bolt holds the first and second intervertebral disk segments together. The bolt may be installed from a position facilitating assembly of the first and second intervertebral disk segments in location between the vertebrae from a posterior surgical approach.

The thickness of the first and second intervertebral disk segments may vary to properly space the adjacent vertebrae apart. In the preferred embodiment, the first intervertebral disk segment is thicker at the anterior-facing edge thereof, becoming progressively thinner toward the posterior-facing side thereof. Similarly, the second intervertebral disk segment is also thicker at the anterior-facing side thereof, becoming progressively thinner toward the posterior-facing edge thereof. This thickness gradient in the intervertebral disk prosthesis of the present invention is designed to help maintain it in place intermediate adjacent vertebrae.

In the preferred embodiment, the first and second intervertebral disk segments and the bolt are all made of a long term biocompatible material such as titanium. If desired, the intervertebral disk prosthesis of the present invention may also be secured in place using an adhesive such as bone cement. In an alternate embodiment, the superior and inferior sides of either or both of the first and second intervertebral disk segments may have a plurality of small spikes extending therefrom to secure the first and second intervertebral disk segments in place intermediate the endplates of the vertebrae.

It may therefore be seen that the present invention teaches an improved intervertebral disk prosthesis which may be used to replace an excised intervertebral disk and restore proper spacing between the two adjacent vertebrae which have had the intervertebral disk removed. The intervertebral disk prosthesis of the present invention is of a design and physical configuration which may be easily installed in place intermediate the endplates of the two adjacent vertebrae via a posterior surgical approach. The intervertebral disk prosthesis of the present invention does not require extensive drilling or other precision shaping of the endplates of the adjacent vertebrae prior to installation. The implant procedure for the intervertebral disk of the present invention also does not require the use of complex tools to install and position the intervertebral disk prosthesis intermediate the two vertebrae.

The intervertebral disk prosthesis of the present invention is implantable in a surgical procedure featuring both reduced implant trauma to the patient and reduced time required for the surgeon to implant the device. The intervertebral disk prosthesis of the present invention is highly resistive to dislodgement once it is initially installed intermediate two vertebrae, and it promotes prompt and permanent ingrowth of bone material intermediate the two adjacent vertebrae to facilitate permanent fusion of the aforesaid vertebrae. The intervertebral disk prosthesis of the present invention is made of biocompatible material compatible with long term implant in the human body, and it may be made in different sizes and configurations to fit a wide variety of patients and different disk locations in the spine.

The intervertebral disk of the present invention is of a construction which is both durable and long lasting, and it requires no maintenance once it is implanted. The intervertebral disk prosthesis of the present invention is also of a simple mechanical design and relatively inexpensive construction to enhance its market appeal and thereby afford it the broadest possible market. Finally, all of the aforesaid advantages and objectives of the intervertebral disk prosthesis of the present invention are achieved without incurring any substantial relative disadvantage.

DESCRIPTION OF THE DRAWINGS

These and other advantages of the present invention are best understood with reference to the drawings, in which.

DETAILED DESCRIPTION OF THE PREFERRED EMBODIMENT

The preferred embodiment of the present invention uses a two-piece intervertebral disk prosthesis which has a plurality of large apertures extending between the superior and inferior sides thereof. The fact that the intervertebral disk prosthesis of the present invention is two pieces which are placed between the endplates of the vertebrae separately and sequentially, and then connected together, makes it easier to implant, particularly from a posterior surgical approach. The large apertures extending therethrough allow the intervertebral disk prosthesis of the present invention to replace a degenerated or ruptured intervertebral disk in a manner which will encourage bone ingrowth to occur following the implant, thereby fusing the two vertebrae on opposite sides of the prosthesis together.

Figures 1, 2, 3, 4, 5, 12:
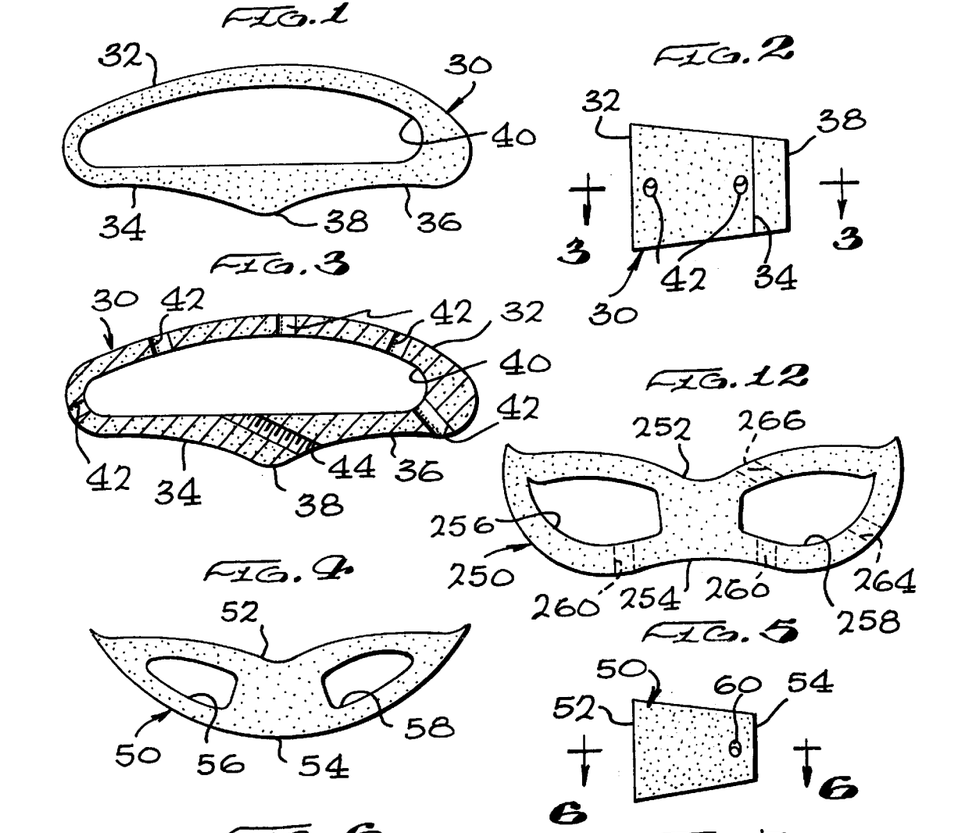
FIG. 1 is a top side (superior) plan view of a first intervertebral disk segment showing a large aperture extending therethrough.
FIG. 2 is a left side view of the first intervertebral disk segment illustrated in FIG. 1, showing that it is thicker at the anterior-facing edge thereof and that it becomes progressively thinner toward the posterior-facing side thereof, and also showing two blood holes extending therethrough.
FIG. 3 is a cross-sectional view of the first intervertebral disk segment illustrated in FIGS. 1 and 2, showing two axially aligned threaded aperture segments located therein and a plurality of blood holes extending therethrough.
FIG. 4 is a top side (superior) plan view of a second intervertebral disk segment showing two large apertures extending therethrough.
FIG. 5 is a left side view of the second intervertebral disk segment illustrated in FIG. 4, showing that it is thicker at the anterior-facing side thereof and that it becomes progressively thinner toward the posterior-facing edge thereof, and also showing a blood hole extending therethrough.
FIG. 12 is a top side (superior) plan view of another alternate embodiment second intervertebral disk segment having a larger configuration in its left/posterior and right/posterior corners thereof.

Referring first to FIGS. 1 through 3, a first intervertebral disk segment 30 which may be made of titanium or some other biocompatible material is illustrated, and will be described as it will be oriented when implanted in a patient. The first intervertebral disk segment 30, which is shown in plan view in FIG. 1 from the superior-facing side thereof (as it will be installed in a patient), has an anterior-facing edge 32, the contour of which forms the half of an elliptical shape lying above the major axis thereof. The posterior-facing edge of the first intervertebral disk segment 30 may be seen as having relatively flat side portions 34 and 36 adjacent the left and right sides of the first intervertebral disk segment 30, respectively. The posterior-facing edge of the first intervertebral disk segment 30 also has a rounded bump 38 which protrudes outwardly (posteriorly) intermediate the flat side portions 34 and 36 at the center of the posterior-facing edge of the first intervertebral disk segment 30.

The first intervertebral disk segment 30 has a large aperture 40 extending therethrough between the superior and inferior sides of the first intervertebral disk segment 30. The large aperture 40 has a contour which is essentially semi-elliptical in configuration (which semi-elliptical configuration is again the half of the elliptical shape which lies above the major axis thereof). The first intervertebral disk segment 30 also has a plurality of blood holes 42 extending through the lateral and anterior sides thereof, the blood holes 42 defining a plurality of paths of fluid communication between the large aperture 40 extending through the first intervertebral segment 30 and the exterior of the first intervertebral disk segment 30 on the lateral and anterior sides thereof.

Referring now only to FIG. 3, the first intervertebral disk segment 30 has a threaded aperture 44 extending through the portion thereof from which the rounded bump 38 protrudes. The threaded aperture 44 extends through the rounded bump 38 at a substantial angle rather than from the posterior side of the rounded bump 38, for reasons that will become more apparent below in conjunction with the discussion of FIGS. 8 and 9, which relate to the installation and placement of the intervertebral disk prosthesis of the present invention intermediate two vertebrae.

Referring now only to FIG. 2, it may be seen that the thickness of the first intervertebral disk segment 30 varies in the preferred embodiment. Specifically, the first intervertebral disk segment 30 is thicker at the anterior-facing facing edge 32 thereof, becoming progressively thinner toward the flat side portions 34 and 36 and the rounded bump 38 at the posterior-facing side thereof.

Figure 6:
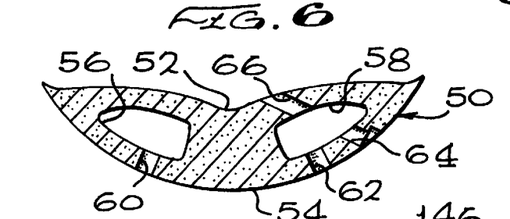
FIG. 6 is a cross-sectional view of the second intervertebral disk segment illustrated in FIGS. 4 and 5, showing two aperture segments located therein and two blood holes extending therethrough.

Referring next to FIGS. 4 through 6, a second intervertebral disk segment 50 which may be made of titanium or some other biocompatible material is illustrated, and it will also be described as oriented when implanted in a patient. The second intervertebral disk segment 50, which is shown in plan view in FIG. 4 from the superior-facing side thereof, has an irregular anterior-facing edge 52. The contour of the anterior-facing edge 52 of the second intervertebral disk segment 50 is configured with a rounded indentation intermediate two relatively flat side portions to closely engage the contour of the rounded bump 38 at the posterior-facing side of the first intervertebral disk segment 30 (illustrated in FIG. 1) when the second intervertebral disk segment 50 is assembled to the first intervertebral disk segment 30.

The second intervertebral disk segment 50 also has a posterior-facing edge 54, the contour of which forms the half of an elliptical shape lying below the major axis thereof. The second intervertebral disk segment 50 has two large apertures 56 and 58 extending therethrough between the superior and inferior sides of the second intervertebral disk segment 50. The large apertures 56 and 58 are located on the left and right sides of the second intervertebral disk segment 50, respectively, and each has a contour which is essentially bullet-shaped in configuration.

The second intervertebral disk segment 50 has a blood hole 60 extending through the posterior side thereof to define a path of fluid communication between the large aperture 56 extending through the second intervertebral disk segment 50 and the exterior of the second intervertebral disk segment 50 on the posterior side thereof. Another blood hole 62 extends through the posterior side of the second intervertebral disk segment 50 to define a path of fluid communication between the large aperture 58 extending through the second intervertebral disk segment 50 and the exterior of second intervertebral disk segment 50 on the posterior side thereof.

Referring now only to FIG. 6, the second intervertebral disk segment 50 has a pair of aperture segments 64 and 66 which extend therethrough and are axially aligned. The aperture segments 64 and 66 extend from a location intermediate the right/posterior side of the second intervertebral disk segment 50. It will be appreciated by those skilled in the art than when the second intervertebral disk segment 50 and the first intervertebral disk segment 30 (illustrated in FIG. 3) are assembled together with the anterior-facing edge 52 of the second intervertebral disk segment 50 in engagement with the flat side portions 34 and 36 and the rounded bump 38 of the first intervertebral disk segment 30, the pair of aperture segments 64 and 66 in the second intervertebral disk segment 50 and the threaded aperture 44 in the first intervertebral disk segment 30 are all axially aligned.

Figure 7:
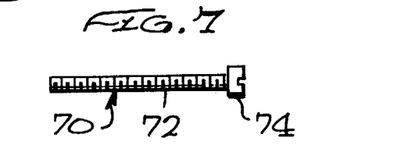
FIG. 7 is a side plan view of a bolt for insertion into the two aperture segments located in the second intervertebral disk segment illustrated in FIGS. 4 through 6, and then to be screwed into the threaded aperture located in the first intervertebral disk segment illustrated in FIGS. 1 through 3.

Referring now to FIG. 7, a bolt 70 having a threaded shaft 72 extending from a bolt head 74 is illustrated. The bolt 70 may be made of titanium or some other biocompatible material. The bolt 70 is for insertion through the pair of aperture segments 64 and 66 in the second intervertebral disk segment 50 (illustrated in FIG. 6), and it may then be screwed into the threaded aperture 44 in the first intervertebral disk segment 30 (illustrated in FIG. 3) to secure the second intervertebral disk segment 50 and the first intervertebral disk segment 30 together.

Figure 8:
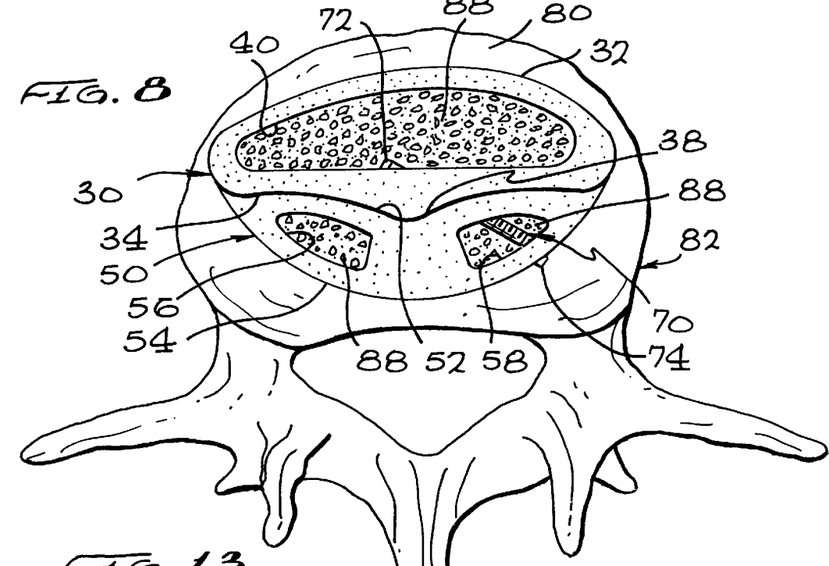
FIG. 8 is a top side (superior) plan view of the first intervertebral disk segment illustrated in FIGS. 1 through 3 and the second intervertebral disk segment illustrated in FIGS. 4 through 6 assembled together with the bolt illustrated in FIG. 7, and located on the superior endplate of a vertebra.
Figure 9:
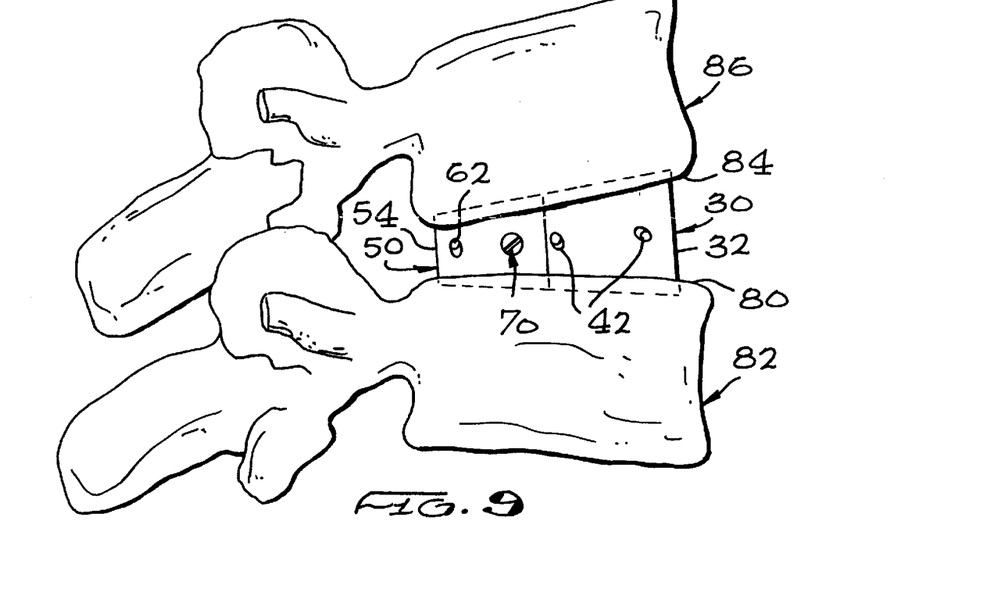
FIG. 9 is a right side view of the intervertebral disk prosthesis illustrated in FIG. 8 installed between two vertebrae.

Referring next to FIGS. 8 and 9, the first intervertebral disk segment 30 and the second intervertebral disk segment 50 are illustrated as being installed intermediate a superior endplate 80 of a first vertebra 82 and an inferior endplate 84 of a second vertebra 86, and secured together with the bolt 70. To install the intervertebral disk prosthesis of the present invention, the first intervertebral disk segment 30 is placed intermediate the superior endplate 80 of the first vertebra 82 and the inferior endplate 84 of the second vertebra 86 in a first step. Then, in a second step, the second intervertebral disk segment 50 is placed intermediate the superior endplate 80 of the first vertebra 82 and the inferior endplate 84 of the second vertebra 86 with the contour of the anterior-facing edge 52 of the second intervertebral disk segment 50 in engagement with the contour of the flat side portions 34 and 36 and the rounded bump 38 at the posterior-facing side of the first intervertebral disk segment 30.

Next, in a third step, the threaded shaft 72 of the bolt 70 is inserted through the pair of aperture segments 64 and 66 in the second intervertebral disk segment 50 (illustrated in FIG. 6), and then screwed into the threaded aperture 44 in the first intervertebral disk segment 30 (illustrated in FIG. 3) to secure the second intervertebral disk segment 50 and the first intervertebral disk segment 30 together intermediate the vertebrae 82 and 86.

Note that since the intervertebral disk prosthesis of the present invention is made in two halves, i.e., the first intervertebral disk segment 30 and the second intervertebral disk segment 50, instead of being made in a single segment, it is easier to install into the area intermediate the vertebrae 82 and 86. This is particularly true if the intervertebral disk prosthesis is being installed from a posterior surgical approach. In addition, with the bolt 70 being inserted into the pair of aperture segments 64 and 66 in the second intervertebral disk segment 50 (illustrated in FIG. 6) and then screwed into the threaded aperture 44 in the first intervertebral disk segment 30 (illustrated in FIG. 3) at the angle illustrated, it will be appreciated by those skilled in the art that it is easy to assemble the intervertebral disk prosthesis of the present invention from a posterior surgical approach.

In the installation procedure, the large aperture 40 in the first intervertebral disk segment 30 and the large apertures 56 and 58 in the second intervertebral disk segment 50 may be filled with bone marrow or with bone chips as indicated by the reference numeral 88. The bone marrow or bone chips 88 will facilitate bone ingrowth through the large aperture 40 in the first intervertebral disk segment 30 and the large apertures 56 and 58 in the second intervertebral disk segment 50 to cause the first vertebra 82 and the second vertebra 86 to fuse together. Note that if desired, bone glue may also be used to retain the first intervertebral disk segment 30 and the second intervertebral disk segment 50 in place intermediate the superior endplate 80 of the first vertebra 82 and the inferior endplate 84 of the second vertebra 86. However, in the preferred embodiment of the present invention, the varied thickness of the first intervertebral disk segment 30 and the second intervertebral disk segment 50 will cause the intervertebral disk prosthesis to be retained intermediate the first vertebra 82 and the second vertebra 86.

Figure 10:
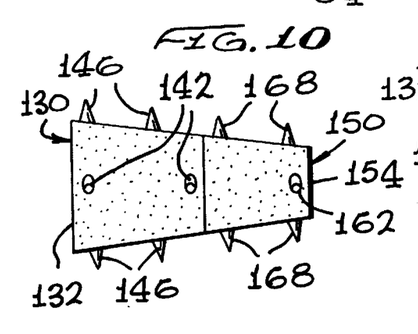
FIG. 10 is a left side view of an assembled alternate embodiment intervertebral disk prosthesis wherein the superior and inferior sides of both of the first and second intervertebral disk segments have a plurality of small spikes extending therefrom to secure the first and second intervertebral disk segments in place intermediate the endplates of vertebrae.
Figure 11:
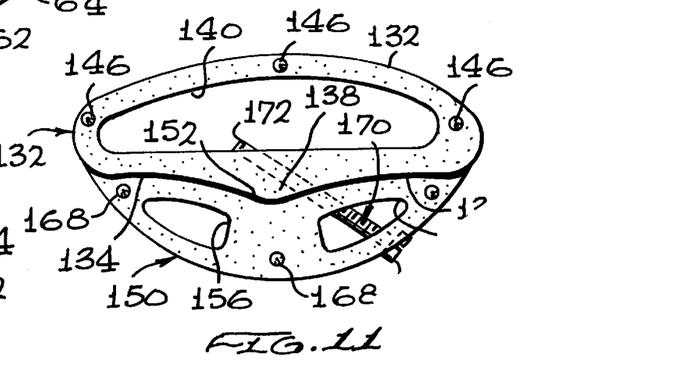
FIG. 11 is a top side (superior) plan view of the assembled alternate embodiment intervertebral disk prosthesis illustrated in FIG. 10.

Referring now to FIGS. 10 and 11, an alternate embodiment is illustrated in which a first intervertebral disk segment 130 and a second intervertebral disk segment 150 are illustrated, which are respectively similar to the first intervertebral disk segment 30 illustrated in FIGS. 1 through 3 and the second intervertebral disk segment 50 illustrated in FIGS. 4 through 6, with reference numerals being identical save for the addition of a "1" prior to each of the components of the first intervertebral disk segment 130 and the second intervertebral disk segment 150. The only difference is that the first intervertebral disk segment 130 has a plurality of small spikes 146 extending from the superior and inferior sides thereof, and the second intervertebral disk segment 150 has a plurality of small spikes 168 extending from the superior and inferior sides thereof. The spikes 146 and 168 are for use to better retain the first intervertebral disk segment 130 and the second intervertebral disk segment 150 in position between the superior endplate 80 of the first vertebra 82 and the inferior endplate 84 of the second vertebra 86.

Referring next to FIG. 12, another alternate embodiment second intervertebral disk segment 250 is illustrated which is similar to the second intervertebral disk segment 50 illustrated in FIGS. 4 through 6, with reference numerals being identical save for the addition of a "2" prior to each of the components of the second intervertebral disk segment 250. The only difference is that the posterior-facing edge 254 of the second intervertebral disk segment 250 has larger configuration left/posterior and right/posterior corners. This configuration will place more of the superior and inferior sides of the second intervertebral disk segment 250 into contact intermediate the inferior endplate 84 of the second vertebra 86 and the superior endplate 80 of the first vertebra 82, respectively.

Figure 13:
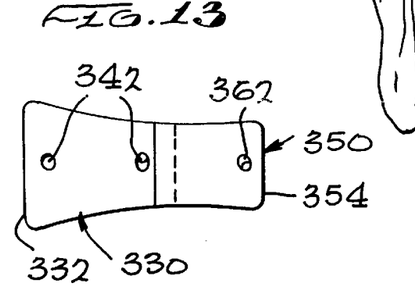
FIG. 13 is a left side view of yet another assembled alternate embodiment intervertebral disk prosthesis wherein the thickness thereof is greater at the anterior and posterior sides thereof than in the area therebetween.

Referring now to FIG. 13, yet another alternate embodiment first intervertebral disk segment 330 and second intervertebral disk segment 350 are illustrated, which are respectively similar to the first intervertebral disk segment 30 illustrated in FIGS. 1 through 3 and the second intervertebral disk segment 50 illustrated in FIGS. 4 through 6, with reference numerals being identical save for the addition of a "3" prior to each of the components of the first intervertebral disk segment 330 and the second intervertebral disk segment 350. The only difference is that the variation in thickness of the first intervertebral disk segment 330 and the second intervertebral disk segment 350 is not continuous. Rather, the intervertebral disk prosthesis is thinner at a location intermediate the anterior and posterior sides thereof than it is at the anterior and posterior edges thereof.

Figure 14:
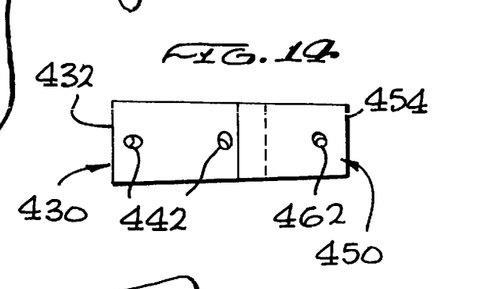
FIG. 14 is a left side view of still another assembled alternate embodiment intervertebral disk prosthesis wherein the thickness thereof is relatively uniform.

Referring finally to FIG. 14, still another alternate embodiment first intervertebral disk segment 430 and a second intervertebral disk segment 450 are illustrated, which are respectively similar to the first intervertebral disk segment 30 illustrated in FIGS. 1 through 3 and the second intervertebral disk segment 50 illustrated in FIGS. 4 through 6, with reference numerals being identical save for the addition of a "4" prior to each of the components of the first intervertebral disk segment 430 and the second intervertebral disk segment 450. The only difference is that the first intervertebral disk segment 430 and the second intervertebral disk segment 450 are of a substantially uniform thickness.

It may therefore be appreciated from the above detailed description of the preferred embodiment of the present invention that it teaches an improved intervertebral disk prosthesis which may be used to replace an excised intervertebral disk and restore proper spacing between the two adjacent vertebrae which have had the intervertebral disk removed. The intervertebral disk prosthesis of the present invention is of a design and physical configuration which may be easily installed in place intermediate the endplates of the two adjacent vertebrae via a posterior surgical approach. The intervertebral disk prosthesis of the present invention does not require extensive drilling or other precision shaping of the endplates of the adjacent vertebrae prior to installation. The implant procedure for the intervertebral disk of the present invention also does not require the use of complex tools to install and position the intervertebral disk prosthesis intermediate the two vertebrae.

The intervertebral disk prosthesis of the present invention is implantable in a surgical procedure featuring both reduced implant trauma to the patient and reduced time required for the surgeon to implant the device. The intervertebral disk prosthesis of the present invention is highly resistive to dislodgement once it is initially installed intermediate two vertebrae, and it promotes prompt and permanent ingrowth of bone material intermediate the two adjacent vertebrae to facilitate permanent fusion of the aforesaid vertebrae. The intervertebral disk prosthesis of the present invention is made of biocompatible material compatible with long term implant in the human body, and it may be made in different sizes and configurations to fit a wide variety of patients and different disk locations in the spine.

The intervertebral disk of the present invention is of a construction which is both durable and long lasting, and it requires no maintenance once it is implanted. The intervertebral disk prosthesis of the present invention is also of a simple mechanical design and relatively inexpensive construction to enhance its market appeal and thereby afford it the broadest possible market. Finally, all of the aforesaid advantages and objectives of the intervertebral disk prosthesis of the present invention are achieved without incurring any substantial relative disadvantage.

Although an exemplary embodiment of the intervertebral disk prosthesis of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. An intervertebral prosthetic disk system for installation intermediate two vertebrae having facing endplates, with anterior and posterior portions said intervertebral prosthetic disk system comprising:

a first intervertebral disk segment for installation intermediate the facing endplates of the two vertebrae, said first intervertebral disk segment having at least one large aperture extending therethrough from a superior side thereof to an inferior side thereof to facilitate bone ingrowth intermediate the two vertebrae, said first intervertebral disk segment being configured for placement in direct contact with a substantial part of the anterior portions of the facing endplates of the two vertebrae;

a second intervertebral disk segment for installation intermediate the facing endplates of the two vertebrae, said second intervertebral disk segment having at least one large aperture extending therethrough from a superior side thereof to an inferior side thereof to facilitate bone ingrowth intermediate the two vertebrae, said second intervertebral disk segment being configured for placement in direct contact with a substantial part of the posterior portions of the facing endplates of the two vertebrae, said first and second intervertebral disk segments being respectively arranged and configured for placement adjacent each other with a posterior-facing edge of said first intervertebral disk segment in engagement with an anterior-facing edge of said second intervertebral disk segment, said first and second intervertebral disk segments, when mutually engaged, together presenting a substantially elliptical configuration parallel to the facing endplates of the two vertebrae; and a mechanical connector for interconnection between said first and second intervertebral disk segments to retain said first and second intervertebral disk segments in mutual engagement adjacent each other following the installation of said first and second intervertebral disk segments intermediate the two vertebrae.

2. An intervertebral prosthetic disk system as defined in claim 1, wherein said first intervertebral disk segment has an anterior-facing edge and a posterior-facing edge, and wherein said second intervertebral disk segment has an anterior-facing edge and a posterior-facing edge, and wherein said posterior-facing edge of said first intervertebral disk segment and said anterior-facing edge of said second intervertebral disk segment are relatively contoured to engage each other when said first and second intervertebral disk segments are in mutual engagement adjacent each other.

3. An intervertebral prosthetic disk system as defined in claim 2, wherein said posterior-facing edge of said first intervertebral disk segment comprises:

a first irregular contour;

and wherein said anterior-facing edge of said second intervertebral disk segment comprises:

a second irregular contour, said first irregular contour of said posterior-facing edge of said first intervertebral disk segment and said second irregular contour of said anterior-facing edge of said second intervertebral disk segment having mutually interlocking configurations.

4. An intervertebral prosthetic disk system as defined in claim 3, wherein said first irregular contour comprises:

a male contour;

and wherein said second irregular contour comprises:

a female contour.

5. An intervertebral prosthetic disk system as defined in claim 3, wherein said first irregular contour comprises:

a rounded bump intermediate two relatively flat side portions;

and wherein said second irregular contour comprises:

a rounded indentation intermediate two relatively flat side portions.

6. An intervertebral prosthetic disk system as defined in claim 3, wherein said first and second intervertebral disk segment are arranged and configured such that said mechanical connector is for interconnection between said first and second irregular contours.

7. An intervertebral prosthetic disk system as defined in claim 1, wherein said first intervertebral segment comprises:

an anterior-facing edge, the contour of which forms the half of an elliptical shape lying above the major axis thereof; and a posterior-facing edge having relatively flat side portions adjacent left and right sides of said first intervertebral disk segment, and a rounded bump which protrudes outwardly intermediate said flat side portions.

8. An intervertebral prosthetic disk system as defined in claim 1, wherein said second intervertebral segment comprises:

an irregular anterior-facing edge having a rounded indentation intermediate two relatively flat side portions; and a posterior-facing edge, the contour of which forms the half of an elliptical shape lying below the major axis thereof.

9. An intervertebral prosthetic disk system as defined in claim 1, wherein said large aperture in said first intervertebral disk segment has a contour which is essentially semi-elliptical in configuration.

10. An intervertebral prosthetic disk system as defined in claim 1, wherein said second intervertebral disk segment has two large apertures extending therethrough the superior and inferior sides of said second intervertebral disk segment, said large apertures in said second intervertebral disk segment being located on left and right sides thereof, respectively.

11. An intervertebral prosthetic disk system as defined in claim 1, wherein said first intervertebral disk segment comprises:

a first plurality of blood holes extending through lateral and anterior sides of said first intervertebral disk segment, said first plurality of blood holes defining a plurality of paths of fluid communication between said large aperture extending through said first intervertebral segment and the exterior of said first intervertebral disk segment on the lateral and anterior sides thereof;

and wherein said second intervertebral disk segment comprises:

a second plurality of blood holes extending through a posterior side of said second intervertebral disk segment, said second plurality of blood holes defining a plurality of paths of fluid communication between said large aperture extending through said second intervertebral segment and the exterior of said second intervertebral disk segment on the posterior side thereof.

12. An intervertebral prosthetic disk system as defined in claim 1, wherein said first intervertebral disk segment comprises:

a threaded aperture extending through a portion thereof;

and wherein said second intervertebral disk segment comprises:

an aperture segment extending through a portion thereof;

and wherein said mechanical connector comprises:

a bolt having a threaded shaft extending from a bolt head, said threaded shaft of said bolt for insertion through said aperture segment in said second intervertebral disk segment and for screwed-in connection into said threaded aperture in said first intervertebral disk segment.

13. An intervertebral prosthetic disk system as defined in claim 12, wherein said aperture segment in said second intervertebral disk segment and said threaded aperture in said first intervertebral disk segment are oriented at an acute lateral angle relative to an axis extending from posterior to anterior.

14. An intervertebral prosthetic disk system as defined in claim 1, wherein the thickness of said first and second intervertebral disk segments varies between an anterior side of said first intervertebral disk segment and a posterior side of said second intervertebral disk segment.

15. An intervertebral prosthetic disk system as defined in claim 14, wherein the thickness of said first and second intervertebral disk segments is thicker at an anterior side of said first intervertebral disk segment than it is at a posterior side of said second intervertebral disk segment.

16. An intervertebral prosthetic disk system as defined in claim 1, additionally comprising:
   a first plurality of small spikes extending from the superior and inferior sides of said first intervertebral disk segment; and
   a second plurality of small spikes extending from the superior and inferior sides of said second intervertebral disk segment.

17. An intervertebral prosthetic disk system as defined in claim 1, wherein said first and second intervertebral disk segments are made of titanium.

18. An intervertebral prosthetic disk system for installation intermediate two vertebrae having facing endplates with anterior and posterior portions, said intervertebral prosthetic disk system comprising:
   a first intervertebral disk segment for installation intermediate the facing endplates of the two vertebrae, said first intervertebral disk segment having an anterior-facing edge and a posterior-facing edge, said first intervertebral disk segment also having at least one large aperture extending therethrough from a superior side thereof to an inferior side thereof to facilitate bone ingrowth intermediate the two vertebrae, said first intervertebral disk segment being configured for placement in direct contact with a substantial part of the anterior portions of the facing endplates of the two vertebrae, said first intervertebral disk segment having a first plurality of blood holes extending through lateral and anterior sides thereof;
   a second intervertebral disk segment for installation intermediate the facing endplates of the two vertebrae, said second intervertebral disk segment having an anterior-facing edge and a posterior-facing edge, said second intervertebral disk segment also having at least two large apertures extending therethrough from a superior side thereof to an inferior side thereof to facilitate bone ingrowth intermediate the two vertebrae, said second intervertebral disk segment being configured for placement in direct contact with a substantial part of the posterior portions of the facing endplates of the two vertebrae, said second intervertebral disk segment having a second plurality of blood holes extending through a posterior side thereof, said posterior-facing edge of said first intervertebral disk segment and said anterior-facing edge of said second intervertebral disk segment being relatively contoured to closely engage each other when said first and second intervertebral disk segments are in mutual engagement adjacent each other, said first and second intervertebral disk segments, when mutually engaged, together presenting a substantially elliptical configuration parallel to the facing endplates of the two vertebrae; and
   a mechanical connector for interconnection between said first and second intervertebral disk segments to retain said first and second intervertebral disk segments in mutual engagement adjacent each other following the installation of said first and second intervertebral disk segments intermediate the two vertebrae.

19. A method of making an intervertebral disk prosthesis for installation intermediate two vertebrae having facing endplates with anterior posterior portions, said method comprising:
   installing at least one large aperture in a first intervertebral disk segment for installation intermediate the facing endplates of the two vertebrae, said large aperture extending through said first intervertebral disk segment from a superior side thereof to an inferior side thereof, said large aperture for facilitating bone ingrowth intermediate the two vertebrae, said first intervertebral disk segment being configured for placement in direct contact with a substantial part of the anterior portions of the facing endplates of the two vertebrae;
   installing at least one large aperture in a second intervertebral disk segment for installation intermediate the facing endplates of the two vertebrae intermediate the facing endplates of the two vertebrae, said large aperture extending through said second intervertebral disk segment from a superior side thereof to an inferior side thereof to facilitate bone ingrowth intermediate the two vertebrae, said second intervertebral disk segment being configured for placement in direct contact with a substantial part of the posterior portions of the facing endplates of the two vertebrae, said first and second intervertebral disk segments being respectively arranged and configured for placement adjacent each other with a posterior-facing edge of said first intervertebral disk segment in engagement with an anterior-facing edge of said second intervertebral disk segment, said first and second intervertebral disk segments, when mutually engaged, together presenting a substantially elliptical configuration parallel to the facing endplates of the two vertebrae; and
   providing a mechanical connector for interconnection between said first and second intervertebral disk segments to retain said first and second intervertebral disk segments in mutual engagement adjacent each other.

20. An intervertebral prosthetic disk system for installation intermediate two vertebrae having facing endplates, said intervertebral prosthetic disk system comprising:
   a first intervertebral disk segment for installation intermediate the facing endplates of the two vertebrae, said first intervertebral disk segment having at least one large aperture extending therethrough from a superior side thereof to an inferior side thereof to facilitate bone ingrowth intermediate the two vertebrae, wherein said first intervertebral disk segment has an anterior-facing edge and a posterior-facing edge, said posterior-facing edge of said first intervertebral disk segment having a first irregular contour comprising a rounded bump intermediate two relatively flat side portions;
   a second intervertebral disk segment for installation intermediate the facing endplates of the two vertebrae, said second intervertebral disk segment having at least one large aperture extending therethrough from a superior side thereof to an inferior side thereof to facilitate bone ingrowth intermediate the two vertebrae, wherein said second intervertebral disk segment has an anterior-facing edge and a posterior-facing edge, said anterior-facing edge of said second intervertebral disk segment having a second irregular contour comprising a rounded indentation intermediate two relatively flat side portions, said first irregular contour of said posterior-facing edge of said first intervertebral disk segment and said second irregular contour of said anterior-facing edge of said second intervertebral disk segment having mutually interlocking configurations which will engage each other when said first and second intervertebral disk segments are placed with said posterior-facing edge of said first intervertebral disk segment and said anterior-facing edge of said second intervertebral disk segment adjacent each other; and
   a mechanical connector for interconnection between said first and second intervertebral disk segments to retain said first and second intervertebral disk segments in mutual engagement adjacent each other following the installation of said first and second intervertebral disk segments intermediate the two vertebrae.

21. An intervertebral prosthetic disk system as defined in claim 20, wherein said first and second intervertebral disk segments, when in mutual engagement with each other, together define a configuration which is substantially elliptical and which is of a size to fit between the facing endplates of the two vertebrae.

* * * * *